(12) United States Patent
Sekura

(10) Patent No.: US 8,290,792 B2
(45) Date of Patent: *Oct. 16, 2012

(54) PRESCRIPTION COMPLIANCE MONITORING SYSTEM

(75) Inventor: Ronald D. Sekura, Key Largo, FL (US)

(73) Assignee: Vivonex, L.L.C., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/090,945

(22) Filed: Apr. 20, 2011

(65) Prior Publication Data

US 2011/0196700 A1 Aug. 11, 2011

Related U.S. Application Data

(63) Continuation of application No. 12/032,185, filed on Feb. 15, 2008, now Pat. No. 7,945,461.

(60) Provisional application No. 60/890,103, filed on Feb. 15, 2007.

(51) Int. Cl.
*G06Q 50/00* (2006.01)
(52) U.S. Cl. .................. 705/3; 705/2; 600/300
(58) Field of Classification Search .............. 705/2–3; 600/300
See application file for complete search history.

(56) References Cited

U.S. PATENT DOCUMENTS

| | | |
|---|---|---|
| 4,725,997 A | 2/1988 | Urquhart et al. |
| 4,748,600 A | 5/1988 | Urquhart |
| 4,768,176 A | 8/1988 | Kehr et al. |
| 4,768,177 A | 8/1988 | Kehr et al. |
| 4,939,705 A | 7/1990 | Hamilton et al. |
| 4,971,221 A | 11/1990 | Urquhart et al. |
| 5,200,891 A | 4/1993 | Kehr et al. |
| 5,642,731 A | 7/1997 | Kehr |
| 5,752,235 A | 5/1998 | Kehr et al. |
| 5,832,448 A | 11/1998 | Brown |
| 5,899,855 A | 5/1999 | Brown |
| 5,933,136 A | 8/1999 | Brown |
| 5,954,641 A | 9/1999 | Kehr et al. |
| 5,956,501 A | 9/1999 | Brown |
| 5,960,403 A | 9/1999 | Brown |
| 5,997,476 A | 12/1999 | Brown |
| 6,018,289 A | 1/2000 | Sekura et al. |

(Continued)

FOREIGN PATENT DOCUMENTS

EP 1 087 322 3/2001

(Continued)

OTHER PUBLICATIONS

U.S. Appl. No. 13/090,962, filed Apr. 20, 2011, Sekura.

(Continued)

*Primary Examiner* — Luke Gilligan
(74) *Attorney, Agent, or Firm* — Oblon, Spivak, McClelland, Maier & Neustadt, L.L.P.

(57) ABSTRACT

A method for monitoring patient compliance to medical therapy that includes repeatedly measuring therapy compliance of a patient, uploading the therapy compliance measurements to a personal computer, connecting a central server using the personal computer, sending the uploaded therapy compliance measurements from the personal computer to the central server, providing a number of predetermined compliance threshold amounts, comparing the sent therapy compliance measurements with the number of predetermined compliance thresholds corresponding to the patient, determining a need and level of intervention based on the result of the comparing and reporting the determined need for intervention to a health professional corresponding to the patient and determined level.

30 Claims, 4 Drawing Sheets

U.S. PATENT DOCUMENTS

| | | | |
|---|---|---|---|
| 6,039,688 A * | 3/2000 | Douglas et al. | 600/300 |
| 6,085,752 A | 7/2000 | Kehr et al. | |
| 6,101,478 A | 8/2000 | Brown | |
| 6,102,855 A | 8/2000 | Kehr et al. | |
| 6,151,586 A | 11/2000 | Brown | |
| 6,161,095 A | 12/2000 | Brown | |
| 6,168,563 B1 | 1/2001 | Brown | |
| 6,270,455 B1 | 8/2001 | Brown | |
| 6,368,273 B1 | 4/2002 | Brown | |
| 6,560,165 B1 | 5/2003 | Barker | |
| 6,822,554 B2 | 11/2004 | Vrijens et al. | |
| 6,968,375 B1 | 11/2005 | Brown | |
| 6,980,958 B1 | 12/2005 | Surwit et al. | |
| 7,340,503 B2 | 3/2008 | Washburn | |
| 7,533,171 B2 | 5/2009 | Brown | |
| 7,624,028 B1 | 11/2009 | Brown | |
| 7,629,889 B2 * | 12/2009 | Sachanandani et al. | 340/573.1 |
| 7,684,999 B2 | 3/2010 | Brown | |
| 7,707,270 B2 | 4/2010 | Brown | |
| 7,822,625 B2 | 10/2010 | Brown | |
| 7,827,040 B2 | 11/2010 | Brown | |
| 7,877,274 B2 | 1/2011 | Brown | |
| 2003/0036683 A1 | 2/2003 | Kehr et al. | |
| 2003/0036923 A1 | 2/2003 | Waldon et al. | |
| 2003/0208465 A1 | 11/2003 | Yurko et al. | |
| 2003/0221687 A1 * | 12/2003 | Kaigler | 128/200.14 |
| 2004/0210458 A1 * | 10/2004 | Evans et al. | 705/2 |
| 2005/0061319 A1 | 3/2005 | Hartley et al. | |
| 2005/0149869 A1 | 7/2005 | Kehr et al. | |
| 2005/0277872 A1 * | 12/2005 | Colby et al. | 604/67 |
| 2006/0089856 A1 | 4/2006 | Kadhiresan et al. | |
| 2006/0154642 A1 | 7/2006 | Scannell, Jr. | |
| 2007/0016443 A1 | 1/2007 | Wachman et al. | |
| 2008/0142472 A1 | 6/2008 | Metry et al. | |

FOREIGN PATENT DOCUMENTS

| | | |
|---|---|---|
| WO | WO 01/87150 | 11/2001 |
| WO | WO 2006/048417 | 5/2006 |

OTHER PUBLICATIONS

"Industry-Leading Technology Expands Remote Patient Care," <http:/www.hctproject.com/documents.asp?d_ID=4175>.

"Monitor Patients Online," <http:/www.memag.com/memag/article/articleDetail.jsp?id=118617>.

"Product Info: Disease Management Coordination Network," <http:/www.ddiofsc.com/product.htm>.

"Web-based Patient Compliance Monitoring," <http:/www.resmed.com/en-us/products/clinical_systems/restraxx_system/documents/restraxx-clinical-fact-sheet-us-english.pdf>.

* cited by examiner

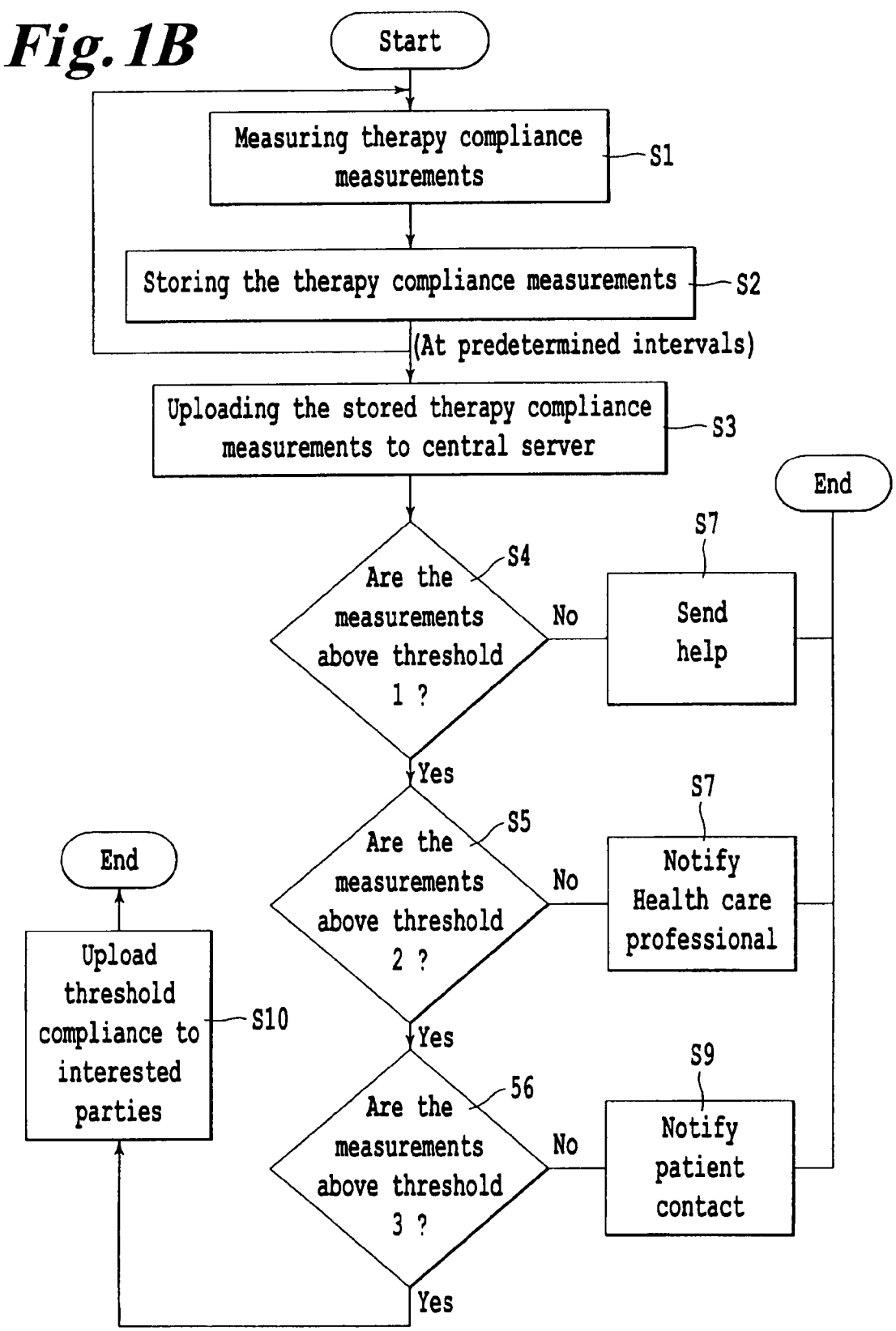

PRESCRIPTION COMPLIANCE MONITORING SYSTEM

CROSS-REFERENCE TO RELATED APPLICATIONS

This application is a continuation of application Ser. No. 12/032,185, filed Feb. 15, 2008 and is also based upon and claims the benefit of priority under 35 U.S.C. §119(e) from U.S. Ser. No. 60/890,103, filed Feb. 15, 2007, the entire contents of which are incorporated herein by reference.

BACKGROUND

In the past it has been difficult to determine if a patient is faithfully following a prescribed therapy, whether it is a prescription drug therapy or physical therapy. Doctors could see how many prescriptions were filled for a user but it was difficult to determine if the patient had actually taken the medicine or walked the distance prescribed. Research has shown that a majority of patients fail to follow their prescribed therapy simply because they forget. A system that measures compliance with a therapy and reports the patient's compliance or non-compliance is needed in order to motivate patients to ensure that they follow their prescribed therapy or to notify a patient's doctor or the authorities if forgetting to take medication would result in a serious medical emergency. Devices that monitor compliance such as that described in U.S. Pat. No. 6,018,289 (incorporated herein by reference) are available; however these devices required the device to be physically monitored in order to determine compliance and were unable to notify caregivers if the patient forgot to take their medication.

SUMMARY OF THE INVENTION

In one embodiment of the present invention, there is provided a method for monitoring patient compliance to medical therapy that includes repeatedly measuring therapy compliance of a patient, uploading the therapy compliance measurements to a personal computer, connecting a central server using the personal computer, sending the uploaded therapy compliance measurements from the personal computer to the central server, providing a number of predetermined compliance threshold amounts, comparing the sent therapy compliance measurements with the number of predetermined compliance thresholds corresponding to the patient, determining a need and level of intervention based on the result of the comparing and reporting the determined need for intervention to a health professional corresponding to the patient and determined level.

BRIEF DESCRIPTION OF THE DRAWINGS

FIGS. 1A and 1B illustrate the prescription compliance monitoring system according to one embodiment of the present invention;

DESCRIPTION OF THE EMBODIMENTS OF THE INVENTION

Figure 1A:
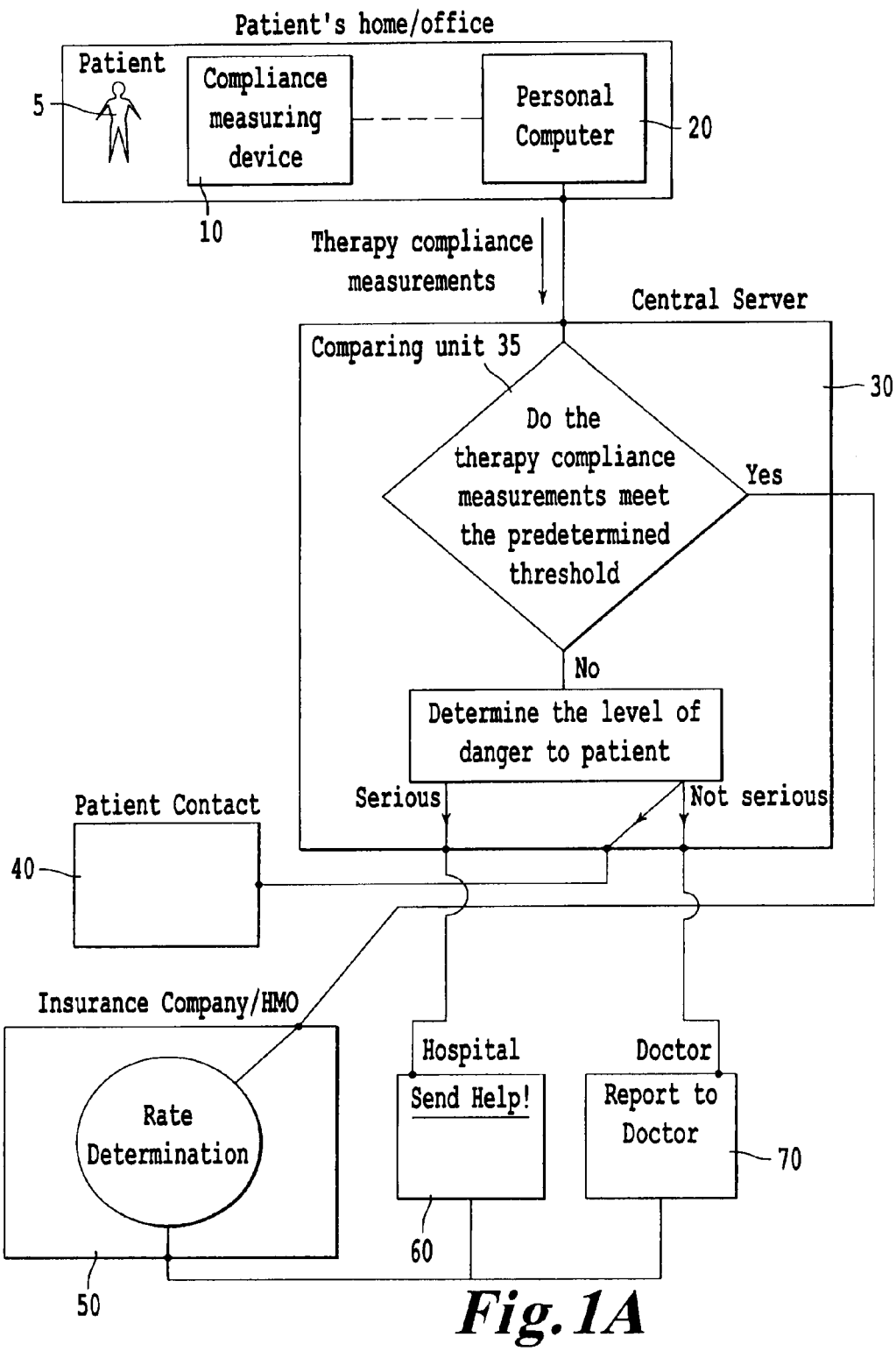

An Internet system is proposed to allow multiple users to access data stored on a central server that is generated on the provider computer and on reminder and monitoring devices used by patients among others. The shared data may include Provider Information, Patient or Client Data, Prescription Regimens or Scheduling Data, Compliance/Adherence Data, Provider Contact Record, and Viewer Contact Record, and Billing Records. The data may be stored at a central server location and stored in SQL Server format. There may be limitations of the data that certain categories of user may view, and these restrictions may vary depending on the specific patient record or data set being reviewed. It should be noted that the system should be HIPPA compliant. The following is an overview of some of the features of an embodiment of the present invention:

A NexDose or similar compliance or adherence and persistence managing application may be installed on a Central server. Also included may be an Administrative application that will permit view and analysis of Provider Contact Record for calculation of reimbursements, and calculation of billing to Insurer or Credit Card. The administrator will be able to activate or inactivate various Provider, Insurer, Viewer, or Patient accounts.

A SQL database houses the various patient or client, and provider and insurer records. A Server to house the SQL database may be provided. The server may operate 24/7 with routine back up.

Parties such as Insurers and Physicians, and others authorized will be permitted to view selected patient/client data and can be automatically contacted via various methods such as, Internet, email, telephone, pager, etc.

The mode for communication between Pharmacist, Physician(s), Insurer and Administrator may be any mode as recognized by one of ordinary skill in the art. For example, the mode may be Email, Phone, Fax, Chat or any other similar type mode of communication.

The system may link to adverse drug interactions database and access to the database may allow upload to database of patient compliance data that is stored on a portable device that can function as a reminder device and as a recording device for timed events and patient/client action in relation to timed events. The device may connect to the central database through a modem or by an Internet connection. Options for direct connection, connection through a computer interface, or wireless connection are also possible.

The system will permit setting of parameters on portable device through the Internet or via a wireless connection.

The system monitors patient/client performance/adherence/compliance to therapy or other prescribed action. The system provides a predetermined metric for monitoring behavior. For each drug or therapy or other area for performance, a performance threshold can be set based on the individual needs or possible dangers resulting from a level of non-compliance. This threshold can be used to alert members of the team to intervene when performance falls below threshold. Failure or success to achieve the threshold value can be used as a metric to: determine a need for intervention; determine continuation of therapy; determine the cost of services or insurance; determine other incentives or penalties that might enhance performances/adherence/compliance/persistence.

The predetermined threshold is calculated as the percentage of times that a therapy is accomplished within a specified interval over the total number of such intervals.

A compliance measurement can include recording a time and action within a specified interval where the action is prescribed to be accomplished. Such action can be positive and denote compliance; negative such as in the example of skipping the prescribed therapy; or negative where there is failure to respond to prescribed therapy. Negative results would be judged as non-compliance.

Examples of instances that can be monitored and compared to compliance thresholds include: taking a dose of medication within a specified interval where many such intervals are scheduled; taking a physiologic measurement within a specified interval where many such intervals are scheduled; meeting with a healthcare provider within a specified interval where many such intervals are scheduled; and performing exercise or physical therapy within a specified interval where many such intervals are scheduled.

Additionally thresholds can be established to document that certain levels of performance are achieved. For example, a patient can be documented to exercise for a set interval; additional thresholds can be set to generate alerts where certain physiologic measurements are not within specified limits or ranges, for example, blood pressure; heart rate; weight; blood glucose; and other such parameters that can be determined by the patient himself and such data stored on the monitoring device.

Instances where failure of compliance can lead to immediate or permanent damage to the patient include: failure to take medication properly for treatment of infectious disease such as HIV infection and bacterial infection; failure to take medication properly that controls diabetes or other hormone related chronic conditions; failure to take medication properly that manages heart and vascular disease; failure to take medication properly that manages neurological condition such as epilepsy, depression and other mental diseases failure to take medication properly that maintains immunosuppression in patients having received transplants; failure to take medication for treatment of renal or respiratory disease; failure to regulate diabetes and other endocrine disease.

Initial Patient Registration is exemplified below in steps 1-8. However, these steps do not have to be performed in the order indicated below.

1—Patient will, according to one embodiment, receive a "prescription" for Medication Therapy Management (MTM), this information will be stored on the records of the Prescription Benefit Manager (PBM). Each time the PBM is contacted regarding the patient's medications an MTM classification will be given. Paper alerts may be used during the filling process to assure that the prescription is delivered in conjunction with the MTM services. As an alternative, a patient may be enrolled in the MTM services directly by themselves, a healthcare provider, an insurer, an employer, a local or federal government agency nonprofit organization, or a hospital.

2—Initial patient registration into the NexDose MTM program (ND-MTM) is initiated by a patient or a Healthcare Team member. Information will be entered into the system that includes patient identification information, medical history, medication or therapy schedules, schedules for monitoring or appointments and additional information specified in a registration form. Registration form data will be stored on the server.

3—Additions to the patient data record may include Insurer Name and Plan Number, Insurer contacts, Physicians with name, ID Number and contact information, Patient identification numbers for Insurers, PBMs, physicians and pharmacists. It may be advisable to produce an electronic form that the Insurer can fill out containing much of this information so that it can be merged in to the MTM system registration document. Information such as disease condition and allergies may be integrated in to the record. It may be desirable to define an alternative contact for the patient. The insurer may also provide a list of medications that the patient is taking.

4—Option for use of NDC number should be initiated. "Each drug product listed under Section 510 of the Federal Food, Drug, and Cosmetic Act is assigned a unique 10-digit, 3-segment number. This number, known as the National Drug Code (NDC), identifies the labeler/vendor, product, and trade package size. The first segment, the labeler code, is assigned by the FDA. A labeler is any firm that manufactures, repacks or distributes a drug product. The second segment, the product code, identifies a specific strength, dosage form, and formulation for a particular firm. The third segment, the package code identifies package sizes. Both the product and package codes are assigned by the firm. The NDC may be in one of the following configurations: 4-4-2, 5-3-2, or 5-4-1." Other identifier options may be included that permit access to drug data on databases developed by third party developers.

5—Updates to registration information and updates to patient regimens and other medical data may be implemented by the designated authorized users. There however should be Administrative override.

6—Registration Data, patient medical information and information about patient regimens will be stored on the central server PC.

7—Event of Initial Patient Registration will be stored on server with Patient, ND-provider, and Insurer identifiers. Confirmation of registration will automatically be sent to Insurer and Providers and other members of the patient Healthcare Team.

8—Download to ND device. This may be accomplished using an interface that connects the device to the server through a PC using an IR interface, through a wireless connection that directly connects the device to the server, or through a device modem line that connects the device to the server over telephone lines.

Patient/Provider Visit is exemplified below in steps 1-6. However, these steps do not have to be performed in the order indicated below.

1—ND-Provider visit may be established via IR-Port, via IR-modem link or via a wireless link for connection of the devices to the sensor. ND provider will connect to the server via the interne for viewing and editing patient records.

2—At Visit, by connecting the device to server through the Internet, the ND-Provider will upload patient compliance data. These data will be stored on the server database 3—Uploaded data will automatically be analyzed by an application resident on the server, using the tabular analysis tool applied over the duration form the last ND-Provider visit. If the level of compliance for any therapy is less than 95% (actual set point to be determined, may vary with therapy or other intervention) a alert will be given informing the ND-Provider to review the data.

4—ND-Provider will review data upon alert. ND-Provider will be given a communications form regarding the alert. The form will identify (in check boxes) to whom notification should be sent (ie Insurer representative and appropriate physician), whether action is required or not (again check boxes). The notification will identify the problematic patient file. Verbiage regarding the issue will be stored on the patient file and will be viewed by the appropriate parties by bringing the patients file up. Documentation of this alert will be stored on the PC and will appropriately be entered on the server data base.

It should be noted that hot mail and cold mail option are available. Hot mail would be an e-mail, page or telephone call that goes out to appropriate parties immediately. Content will be on the patients record but notification of issue will be immediate. Cold mail would be a notification that is put on the patient record that would be seen when ND-Provider or a visitor signs on to the system. For example, a new prescription is given and the patient is instructed to stop taking a another medication. There should be flags (may be for doctors or patients) that allow a message to remain active or inactive each time a particular user signs on to the patient record.

5—At visit ND-Provider may adjust regimens and/or medications. These data will be entered onto a server database and will be downloaded to the NexDose Device. Confirmation of download should be stored on the server.

6—Events of Data Upload, Regimen Download, Alerts, and Communications should be stored on the server data base in conjunction with appropriate identifiers.

Viewer(Physician)/Patient Web Visit is exemplified below in steps 1-4. However, these steps do not have to be performed in the order indicated below.

1—If a Physician opts to act as a patient healthcare team member he will be able to act as a ND-Provider or as a viewer. Provider functionality is as described above.

2—As a Viewer the physician will have access to the patients Active Profile. If presented with the NexDose device he will be able to Upload compliance data and use the ND tools evaluate the patient. The physician will also be able to generate and read Hot and Cold Mail.

3—Physicians (or other authorized user) not owning NexDose PC software will be able to log onto the NexDose web site. User ID information will be required to gain access to a particular Patient's Data. When signed onto the patients record these users will be able to review that Active Profile, use server based tools to evaluate patient compliance data, and generate and read Hot and Cold Mail, and if given authorization, modify Patient Regimes.

4—A record of registered user review of a particular patients file will be kept on the server with appropriate identifiers.

Other Registrations

1—Patient Login: Patients will be able to connect their NexDose Device to the server by establishing a wireless (IR, Bluetooth, etc.) connection with a PC connected to the Internet; by using a wireless connection to a modem that connects to the server; or by having a NexDose device that makes a direct wireless connection to the server. Once connected to the server, monitoring data stored in the device will be uploaded to the server, and new information about regimen schedules, changes in medication will be downloaded to the device. Patients will be given the option to login to the Internet and view their information that is stored on the server database. Patients will only have access to their data when signed into the Internet application.

2—ND-Providers: May sign on to web, they will have many patients they serve. Access will be limited to only those patients for whom they are the designated ND-Provider. It is envisioned that a ND-Provider may include many individual users, sometimes at different locations. Constraints at the level of the Internet application will define each individual's activities. Safe guards may be put in place to assure that most recent modifications to the Patient's regimens have been updated to the server. Registration for these users will include Entity Name, Listed Locations, and Listed Users. Along with appropriate numeric identifiers. Sign on will require codes that identify entity and location, and user. The user may also enter a password that is periodically updated.

3—Viewers/Physicians: Will have many patients they serve. Access may be limited to only those patients for whom they are the designated physician. Safe guards may put in place to assure that more recent modifications to the Patient's regimens have been updated to the server. Activity will be to view Active Profile, Evaluate Compliance Data, and Participate in Hot and Cold mail. Registration for these users will include Entity Name, Listed Locations, Listed Users. Along with appropriate numeric identifiers. Sign on will require codes that identify entity and location, and user. The user may also enter a password that is periodically updated.

4—Insurers: Will have many patients they serve. Access may be limited to only those patients for whom they are the designated Insurer. Consideration must be given to the ownership of multiple Insurance Providers by a single conglomerate. Insurers will provide a MTM prescriptions and perhaps initiate a patient registration form (The Form can be given a unique identifier so that the ND-Provider of the Patient's choice can locate it by signing onto the web site). Other activities will be similar to those given to Viewers/Physicians above. The insurer will not be able to alter patient data or regimens. This may be done by the designated providers. The Insurer may be able to access data for all of its clients for and statistical analysis. Consideration is given to removal of patient identifiers for this analysis. Registration for these users may include Entity Name, Listed Locations, Listed Users. Along with appropriate numeric identifiers. Sign on will require codes that identify entity and location, and user. The user may also enter a password that is periodically updated.

5—Administrators: Will operate at the level of maintaining the data base. Web site access to provide these services would be advisable. Administrators would make updates to software, add or delete Insurers and ND-Providers, manage the registration for Viewers, Providers, Insurers, and Administrators. Tools that facilitate global replacement of physician, insurer representatives and viewers for certain patient groups may be added. Additionally tools that calculate patient visits and or activities for proper reimbursement of ND-Providers and proper billing or insurers may be added. Mechanisms are put in place to reconcile billing and payment records. Tools to evaluate overall activity on logged in web site may be added. It should be noted that clients independent of insurers may desire to obtain services.

The Web Site may include the following components:

1—A NexDose web page may be the platform for the envisioned enhancements.

2—Under the Providers Tab the following sub categories may be installed: List of ND-Providers; NexDose Sign On 3—List of ND-Providers tab will provide a list of providers sorted by State and City. It should be possible to search this data base by Zip Code or by area code and exchange. This list will start very small but will grow and be in frequent flux.

4—Sign on will deliver user to pages appropriate for their registration classification. Provider, Viewer, Insurer, Administrator. Consideration should be given that an individual may function with different patients in different capacities.

5—Sign on to an individual patients records will only be permitted to individuals or entities identified in the patient record.

6—ND-Providers and Insurers will be given the option to enter data into the New
Patient registration form. Forms filled by insurers will be given a code so they can be accessed by patient identified ND-Providers.
7—Mechanisms for locating specific records by different users to be discussed.

IR Modem

1—IR-Modem will communicate with the patients portable device (such as ND-Device) from a remote location to a PC. The data will be stored on PC and then uploaded to the central Server at regular intervals or immediately.
2—PC interface to the central sever can be via a proprietary program, via the internet, via XML or other similar type communications protocol.

Home Care

1—Visiting health care providers may travel with PC to patients home. Data may be stored on PC then uploaded to the central Server or be immediately uploaded to the server via an Internet connection.
2—Other types of data that can be monitored to measure compliance are: Temperature, Blood Pressure, Pulse Rate, Weight, Cholesterol, Glucose, Insulin, among others. It is also possible to use the system to monitor and/or schedule patient visits to healthcare providers, participate in exercise programs, diet programs and other health related activities.
3—Also available are tools for programming the patient's portable monitoring device (such as ND Device or other devices) and for Data analysis. In addition the monitoring device could be a non-portable device such as an IR scanner or other similar device that would be connected to the PC. In addition, if the case that a portable monitoring device is used several different types of wireless communication can be used to communicate the data from the device to the PC or directly to the central server such as wireless, wifi, cellular networks, radio, microwave, WiMAX, Bluetooth, ultra-wideband or other similar type connections.

Referring now to the drawings wherein like reference numbers designate identical or corresponding parts throughout the several views and more particularly to FIGS. 1A-B thereof, there is shown an illustrative example of the prescription compliance monitoring system of the present invention. In FIG. 1A there is shown a patient 5 and a corresponding prescription compliance measuring device 10 which may correspond to the NexDose device. Using the device 10, patient 5 compliance with a therapy regimen is tracked and stored. At an allotted time or based on some other factor such as distance or availability the device 10 uploads the compliance data to the personal computer 20. The connection between the device 10 and the personal computer 20 may be wireless, via a docking station, over the internet, over a mobile network, etc. The personal computer 20 then contacts a central server 30 and uploads the compliance data along with data identifying the device 10 and/or the patient 5. The central server 30 then utilizes a comparing unit 35 to compare the compliance data against at least one predetermined threshold in order to determine compliance. The threshold can be generic or based on specific data regarding the patient in question. In addition, the predetermined threshold can be a result of a mathematical computation that takes into account historical data on the patient or a group of patients.

If the result of the comparison is that the patient 5 has complied with his/her therapy regimen, this data is forwarded onto the insurance company 50 to enable the insurance company 50 to make a rate determination, for example. However, if the result of the comparison is that the patient 5 has not complied with his/her therapy regimen a second step of determining the level of danger to the patent is executed. This determination can be based on a threshold difference value, such as how great is the delta between the predetermined threshold and the patient's compliance data. Alternatively or in addition, the determination can be based on personalized data that takes into account the individualized risk that the patient faces due to non-compliance with the therapy regimen. For example, if the patient relies on insulin shots in order to avoid diabetic shock, missing even one treatment could result in danger depending on the severity of the patient's 5 condition.

If it is determined that the danger to the patient exists this is reported to a heath care professional such as a hospital 60 or a similar emergency heath care agent. This data is also eventually forwarded onto the insurance company 50. Alternatively, if it is determined that there is no immediate danger to the patient 5, the data can be forwarded onto the patient's 5 doctor 70 or to a predetermined patient contact 40. This receiving party is then able to deal with the non-compliance in due time. In addition, this data is also eventually forwarded onto the insurance company 50.

In an alternate embodiment illustrated in FIG. 1B, the flow begins at step S1 where therapy compliance measurements are measured. This measurement will preferably be accomplished using a prescription compliance device such as the NexDose device but could also be accomplished using any suitable other device. Next the therapy compliance measurements are stored in step S2. This storing can be locally on the monitoring device or can be at a local PC or on the internet etc. The stored measurements are then uploaded to a central sever at predetermined intervals in step S3. Alternatively, the measurements can be uploaded to the central server immediately upon measurement. This would result in the compliance measurement device acting as a thin-client.

The measurements are then processed to determine a compliance measurement value and compared against a first threshold in step S4. If the compliance measurement value is above the first threshold then the flow moves to step S5. If the compliance measurement value is not above a first value, then the flow moves to step S7 where help is sent to the patient.

In step S5 the compliance measurement value is compared against a second threshold. If the compliance measurement value is above the second threshold then the flow moves to step S6. If the compliance measurement value is not above the second value, then the flow moves to step S8 where a heath care professional such as the patient's doctor is notified of the event.

In step S6 the compliance measurement value is compared against a third threshold. If the compliance measurement value is above the third threshold then the flow moves to step 10 where the threshold compliance is uploaded to interested parties. If the compliance measurement value is not above the second value, then the flow moves to step S9 where a patient contact is notified of the event.

Figure 2:
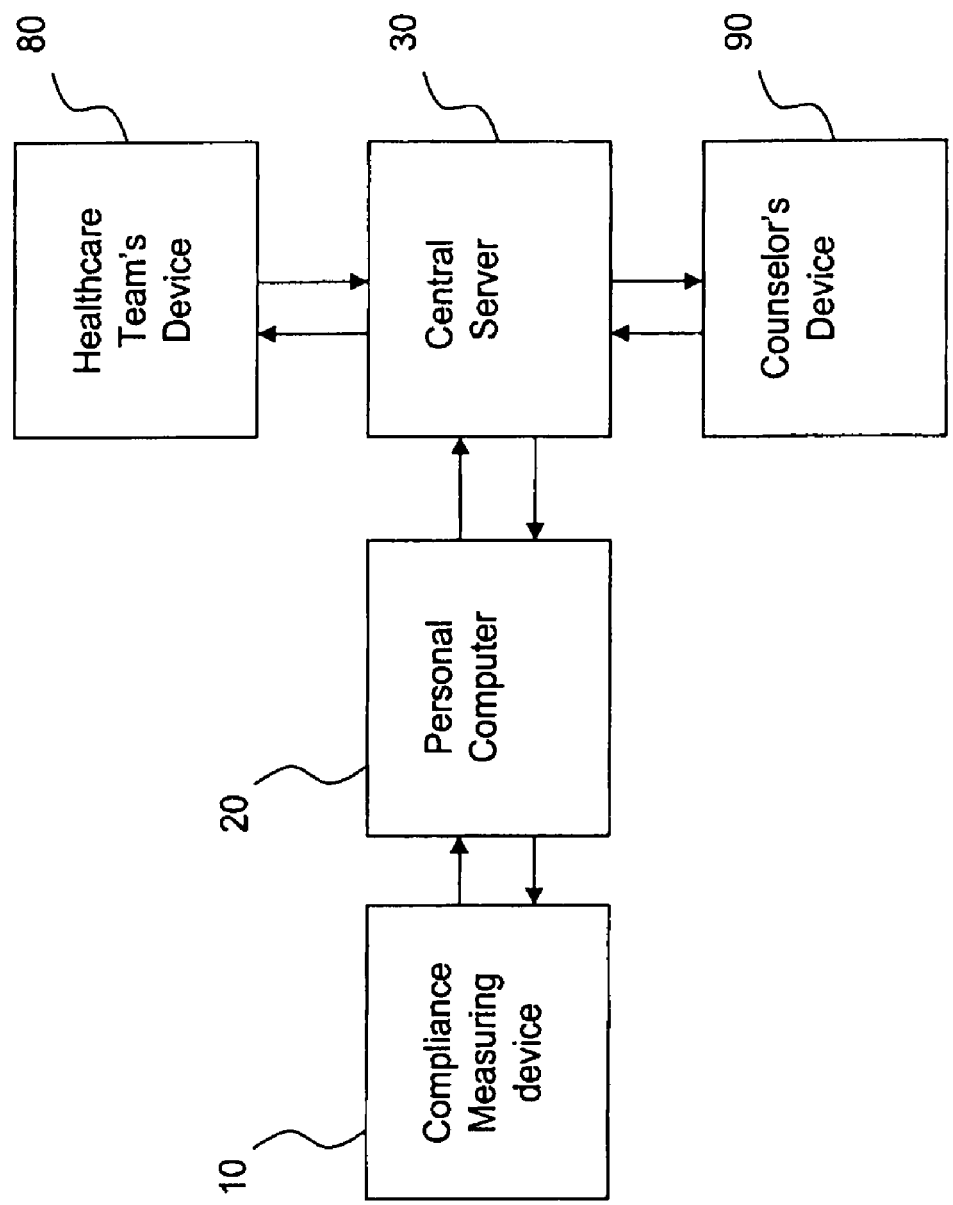
FIG. 2 shows an illustration of the set-up for the counseling portion of the compliance monitoring system of the present invention.

FIG. 2 illustrates another embodiment of the present invention. Specifically, this embodiment illustrates the ability of a counselor or another member of a patient's 5 healthcare team to access the therapy compliance measurements via the central server 30. Specifically, the healthcare team's device 80 is able to connect via a network, such as the interne etc, to the central server 30 where the compliance measurements can be viewed. In addition, a counselor's device 90 is also able to access the compliance measurements. This could be useful if a patient's counselor wishes to check-up on the patient.

Figure 3:
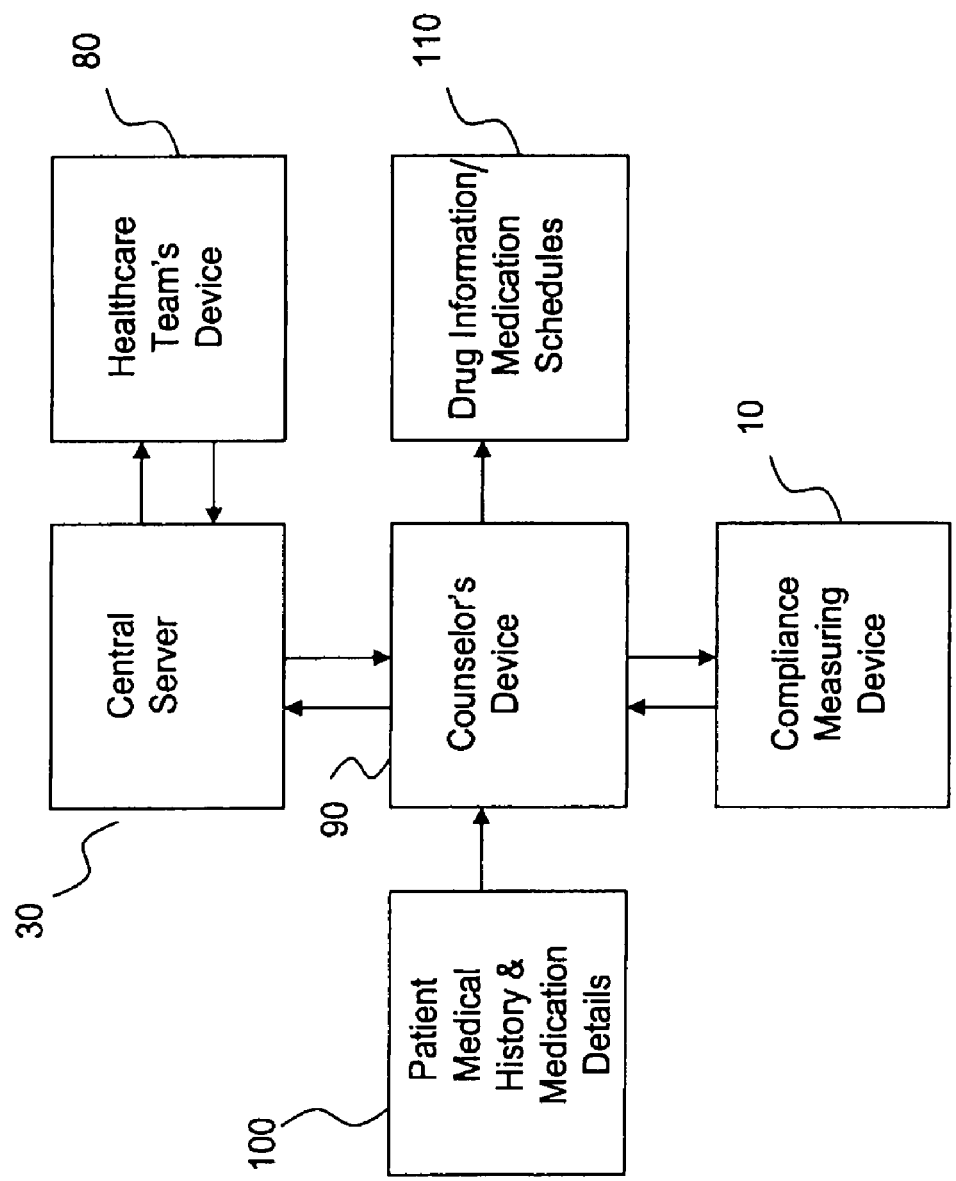
FIG. 3 illustrates the compliance monitoring system according to another embodiment of the present invention.

It is also possible that the compliance measuring device 10 can be connected to the counselor's device directly. This embodiment is illustrated in FIG. 3. In addition, FIG. 3 illustrates that other information such as patient medial history and medication details 100 can be also sent to the counselor's device 90 along with drug information and medication schedules 110. Once a counseling session is complete, data received from the compliance measuring device 10 as well as the counseling session can be uploaded to the central server 30 where the data can be accesses by a healthcare team's device 80 or by the counselor at a later date.

The present invention is not limited to the specifically disclosed embodiments, and variations and modifications may be made without departing from the scope of the present invention.

The invention claimed is:

1. A method for monitoring patient compliance to medical therapy using a device having a central processing unit and a server having a central processing unit, comprising:
   receiving therapy compliance measurements of a patient repeatedly measured by obtaining a voluntary compliance response from the patient using the device;
   selecting, using the server, a number of individualized compliance threshold amounts for the patient, the individualized compliance threshold amounts being uniquely selected for the patient based on characteristics of the medical therapy;
   comparing, using the server, the received therapy compliance measurements with the number of individualized compliance thresholds corresponding to the patient;
   identifying, using the server, instances where patient compliance fails to meet the individualized compliance thresholds; and
   reporting a failure to meet the individualized compliance thresholds to a care-giving party enabling action to be taken by that party.

2. The method according to claim 1, wherein the medical therapy includes at least one of: reminders for exercise and physical therapy, reminders to record vital sign data, reminders to record symptom severity for a medical condition, reminders for medical appointments, and reminders to record results for patient use tests.

3. The method according to claim 1, wherein the actions taken by that party include providing rewards.

4. The method according to claim 1, wherein the actions taken by that party include implementing patient cost increases.

5. The method according to claim 1, wherein a capacity to record voluntary responses and a capacity to transfer corresponding data to the server are both resident in the device.

6. The method according to claim 1, wherein the medical therapy includes a recordation of medical information regarding the patient.

7. The method according to claim 1, wherein the medical therapy includes performance of an anaerobic activity.

8. A method for monitoring patient compliance to medical therapy using a device having a central processing unit and a server having a central processing unit, comprising:
   receiving therapy compliance measurements of a patient repeatedly measured by obtaining a voluntary compliance response from the patient using the device;
   selecting, using the server, a number of individualized compliance threshold amounts for the patient, the individualized compliance threshold amounts being uniquely selected for the patient based on characteristics of the medical therapy;
   comparing, using the server, the received therapy compliance measurements with the number of individualized compliance thresholds corresponding to the patient;
   identifying, using the server, instances where patient compliance meets the individualized compliance thresholds; and
   reporting a success in meeting the individualized compliance thresholds to a care-giving party enabling action to be taken by that party.

9. The method according to claim 8, wherein the medical therapy includes at least one of: reminders for exercise and physical therapy, reminders to record vital sign data, reminders to record symptom severity for a medical condition, reminders for medical appointments, and reminders to record results for patient use tests.

10. The method according to claim 8, wherein the actions taken by that party include providing rewards.

11. The method according to claim 8, wherein the actions taken by that party include implementing patient cost increases.

12. The method according to claim 8, wherein a capacity to record voluntary responses and a capacity to transfer corresponding data to the server are both resident in the device.

13. The method according to claim 8, wherein the medical therapy includes a recordation of medical information regarding the patient.

14. The method according to claim 8, wherein the medical therapy includes performance of an anaerobic activity.

15. A server for monitoring patient compliance to medical therapy having a central processing unit, comprising:
   a reception unit configured to receive therapy compliance measurements of a patient repeatedly measured by obtaining a voluntary compliance response from the patient using a device;
   a selection unit implemented by the central processing unit and configured to select a number of individualized compliance threshold amounts for the patient, the individualized compliance threshold amounts being uniquely selected for the patient based on characteristics of the medical therapy;
   a comparison unit configured to compare the received therapy compliance measurements with the number of individualized compliance thresholds corresponding to the patient;
   an identification unit configured to identify instances where patient compliance fails to meet the individualized compliance thresholds; and
   a reporting unit configured to report a failure to meet the individualized compliance thresholds to a care-giving party enabling action to be taken by that party.

16. The server according to claim 15, wherein the therapy compliance measurements are received via wireless connection.

17. The server according to claim 16 wherein the wireless connection is one of IR, Bluetooth, cellular and/or wireless local area network.

18. The server according to claim 15, wherein the therapy compliance measurements are received via wired connection.

19. The server according to claim 15, wherein the device is a NexDose device, a device containing compliance measurement software installed thereon, a cellular phone, a smart phone, a tablet computer, a notebook computer, or a personal computer.

20. The server according to claim 19, wherein a capacity to record voluntary responses and a capacity to transfer corresponding data to the server are both resident in the device.

21. The server according to claim 15, wherein the therapy compliance measurements are integrated into a medical record or an insurance record.

22. The server according to claim 15, wherein a capacity to record voluntary responses and a capacity to transfer corresponding data to the server are both resident in the device.

23. A server for monitoring patient compliance to medical therapy having a central processing unit, comprising:
- a reception unit configured to receive therapy compliance measurements of a patient repeatedly measured by obtaining a voluntary compliance response from the patient using a device;
- a selection unit implemented by the central processing unit and configured to select a number of individualized compliance threshold amounts for the patient, the individualized compliance threshold amounts being uniquely selected for the patient based on characteristics of the medical therapy;
- a comparison unit configured to compare the received therapy compliance measurements with the number of individualized compliance thresholds corresponding to the patient;
- an identification unit configured to identify instances where patient compliance meets the individualized compliance thresholds; and
- a reporting unit configured to report success in meeting the individualized compliance thresholds to a care-giving party enabling action to be taken by that party.

24. The server according to claim 23, wherein the therapy compliance measurements are received via wireless connection.

25. The server according to claim 24 wherein the wireless connection is one of IR, Bluetooth, cellular and/or wireless local area network.

26. The server according to claim 23, wherein the therapy compliance measurements are received via wired connection.

27. The server according to claim 23, wherein the device is a NexDose device, a device containing compliance measurement software installed thereon, a cellular phone, a smart phone, a tablet computer, a notebook computer, or a personal computer.

28. The server according to claim 27, wherein a capacity to record voluntary responses and a capacity to transfer corresponding data to the server are both resident in the device.

29. The server according to claim 23, wherein the therapy compliance measurements are integrated into a medical record or an insurance record.

30. The server according to claim 23, wherein a capacity to record voluntary responses and a capacity to transfer corresponding data to the server are both resident in the device.

* * * * *